United States Patent [19]

Levy et al.

[11] Patent Number: 5,094,661
[45] Date of Patent: Mar. 10, 1992

[54] CALCIFICATION-RESISTANT MATERIALS AND METHODS OF MAKING SAME THROUGH USE OF TRIVALENT ALUMINUM

[75] Inventors: Robert J. Levy; Amnon Sintov, both of Ann Arbor, Mich.

[73] Assignee: The University of Michigan, Ann Arbor, Mich.

[21] Appl. No.: 176,789

[22] Filed: Apr. 1, 1988

[51] Int. Cl.$^5$ ............ A61L 17/00; A63B 51/02
[52] U.S. Cl. ............ 8/94.11; 8/94.29; 623/1; 623/2; 623/11; 623/22
[58] Field of Search ......... 8/94.11, 404, 94.29; 623/1, 2, 11, 22

[56] References Cited

U.S. PATENT DOCUMENTS

| | | | |
|---|---|---|---|
| 713,046 | 11/1902 | Amend | 8/94.29 |
| 725,648 | 4/1903 | Amend | 8/94.29 |
| 2,750,251 | 6/1956 | Bloch et al. | 8/94.11 |
| 3,650,141 | 2/1971 | Kurilla et al. | 8/94.11 |
| 3,922,356 | 11/1975 | Cohly | 8/94.11 |
| 4,097,234 | 6/1978 | Sohde et al. | 8/94.19 |
| 4,481,009 | 11/1984 | Nashef | 8/94.11 |
| 4,597,960 | 7/1986 | Cohen | 424/435 |
| 4,753,652 | 6/1988 | Langer | 8/94.11 |
| 4,770,665 | 9/1988 | Nashef | 8/94.11 |

*Primary Examiner*—Prince Willis, Jr.
*Assistant Examiner*—John F. McNally
*Attorney, Agent, or Firm*—Rohm & Monsanto

[57] ABSTRACT

Bioprosthetic materials, either natural or synthetic, are treated with trivalent aluminum cations to prevent in vivo calcification. Such bioprosthetic materials include porcine aortic valve leaflets, bovine pericardium, aortic homografts, biocompatible elastomers, and the like which are intended for invasive, or in-dwelling use in a human or animal body. Simple incubation of the natural bioprosthetic materials in an aluminum ion-containing solution, such as aqueous $AlCl_3$, prior to implantation has been found to inhibit calcification of the biomaterial over a prolonged period and to do so without adverse side effects. Incorporation of an aluminum-containing compound into the formulation for polymers, such as polyurethane, has also been found to inhibit calcification with no adverse side effects.

1 Claim, No Drawings

CALCIFICATION-RESISTANT MATERIALS AND METHODS OF MAKING SAME THROUGH USE OF TRIVALENT ALUMINUM

This invention was made with government support under Contract 5-R01-HL38118 awarded ny the National Heart, Lung and Blood Institute within the National Institutes of Health. The federal government has certain rights in the invention.

BACKGROUND OF THE INVENTION

This invention relates generally to materials which are resistant to in vivo calcification, and more particularly, to the treatment of biocompatible polymeric materials, synthetic or natural, such as bovine pericardium, porcine heart valves or homografts, with trivalent aluminum cations as the anticalcification agent.

The life expectancy of patients with severe cardiac valve disease is limited, often valve replacement surgery is the only means of treating the problem. However, at the present time, there are no replacements for diseased heart valves which are totally problem free. Current replacement valves include mechanical valves entirely composed of synthetic polymeric material such as polyurethane; bioprosthetic valves derived from glutaraldehyde-pretreated bovine pericardium or porcine aortic valves; and aortic homografts.

Use of mechanical valves is frequently complicated by thrombosis and tissue overgrowth leading to valvular failure. Calcification, however, has emerged as the most frequent cause of the clinical failure of bioprosthetic heart valves fabricated from porcine aortic valves or bovine pericardium. Human aortic homograft implants have also been observed to undergo pathologic calcification involving both the valvular tissue as well as the adjacent aortic wall albeit at a slower rate than the bioprosthetic heart valves. Pathologic calcification leading to valvular failure, in such forms as stenosis and/or regurgitation, necessitates re-implantation. Therefore, the use of bioprostheses heart valves and homografts has been limited because such tissue is subject to calcification. Pathologic calcification also complicates the use of synthetic vascular grafts and other artificial heart devices such as pacemakers.

Bioprosthetic heart valves from glutaraldehyde-pretreated bovine pericardium or porcine aortic valves provide blood flow characteristics which closely approximate physiologic. Moreover, use of these bioprostheses is accompanied by low incidence of thrombosis, and hence, does not require the administration of anticoagulants. Thus, bioprostheses are preferred for use, particularly in active children and adolescents. Unfortunately, while calcification of bioprostheses has caused valve failure in patients of all ages, there is a greater incidence in children and young adults. Over 50% of all reported valve implants placed in children under the age of 15 years at the time of initial implantation result in bioprosthesis failure due to calcification within 5 years. In comparison, porcine aortic valve bioprostheses implanted in adults have about a 20% incidence of failure due to calcification after 10 years. Efforts to provide long term inhibition of calcification have been unsuccessful to date. Currently, the problem of valve failure has prevented the widespread use of such bioprostheses even in those patients who could benefit significantly therefrom.

Research on the inhibition of calcification has focussed on tissue pretreatment with either detergents or diphosphonates. Both of the aforementioned compounds tend to wash out of the bioprosthetic tissue with time due to blood-material interactions. Thus, these treatments merely delay the onset of the inevitable calcification process. To date, long-term prevention of calcification has been an unattainable result. Accordingly, there is a need for a long-term anticalcification agent for incorporation into bioprosthetic heart valves and the like.

The mechanism for pathological calcification of cardiovascular tissue is not understood. Generally, the term pathologic calcification refers to the deposition of calcium phosphate mineral salts in association with a disease process. Calcification may be due to host factors, implant factors and extraneous factors such as mechanical stress. There is some evidence to suggest that deposits of calcium are related to devitalized cells, especially membrane cells, where the calcium pump ($Ca^{+2}$-$Mg^{+2}$-ATPase) responsible for maintaining low intracellular calcium levels is no longer functioning. Calcification has been observed to begin with an accumulation of calcium and phosphorous, present as hydroxyapatite, which develops into nodules that can eventually lead to valvular failure.

We have discovered that trivalent aluminum cations prevent in vivo calcification of biomaterials. There are no known examples in the prior art of the use of trivalent aluminum cations to inhibit calcification of biomaterials.

Although aluminum is one of the most abundant elements occurring in nature, it plays no biologic role in human physiology. Aluminum has been used for medicinal purposes for many years and can be found in antacids, antiperspirants, acne medications, antidiarrheals, and products used to treat insect bites and stings. Such aluminum-containing products show no toxicity when applied topically, but high doses of antacids have been known to cause metabolic disturbances, including gastrointestinal absorption of aluminum. Aluminum toxicity, including severe dementia and osteomalacia, has been observed in patients receiving long term hemodialysis. The osteomalacia has been observed to correlate with ineffective calcium phosphate mineral deposition in the bones. The trivalent cation of aluminum ($Al^{+3}$), found in trace amounts in intravenous fluid preparations, has been associated with altered bone mineralization and osteomalacia.

It is therefore an object of the invention to provide biomaterials for implantation in a human or animal body having increased resistance to pathologic calcification.

It is another object of the invention to provide biomaterials which will permit the widespread use of bioprosthetic heart valves with a reduced risk of valvular failure.

It is further object of the invention to provide biomaterials exhibiting calcification inhibition locally thereby avoiding the toxic systemic side effects of anticalcification agents, such as aluminum, which can result in growth retardation and calcium imbalance.

It is yet another object of the invention to provide biomaterials having a long-term, or prolonged, anticalcification effect.

SUMMARY OF THE INVENTION

The foregoing and other objects are achieved by this invention wherein trivalent aluminum cations are incorporated on a substrate material which may be a synthetic organic polymer such as polyester, polytetrafluoroethylene, polyurethane, nylon or silastic or other silicone-based material or a biological material such as bovine pericardium, porcine aortic leaflets, and aortic homografts.

In a method aspect of the invention, the substrate material is subjected to a solution containing trivalent aluminum cations. In the case of synthetic polymers, an aluminum-containing compound may be incorporated in the polymeric structure by inclusion in a solvent casting technique or by addition to the polymer precursors so that it is incorporated in the solid state polymer.

DETAILED DESCRIPTION OF THE INVENTION

Calcification-resistant materials can be prepared by various techniques which complex trivalent aluminum ions with a substrate biomaterial. The word "complex" is used herein broadly to indicate some form of combination wherein the aluminum ions are bound to, incorporated on, or in, the substrate biomaterial in such a manner as to provide anticalcification effects over a sustained period of time.

The mechanism of $Al^{+3}$ in inhibiting calcification is unknown. However, the trivalent cation should have the ability to form strong ionic bonds with negatively charged phosphate groups, as well as other negatively charged residues, in the collagen fibrils of bioprosthetic tissue, for example. Such ionic bonds could inhibit the formation of calcium phosphate nuclei in the tissue. Bound $Al^{+3}$ may also cause stearic inhibition of calcium deposition. A strong ionic bond formed between $Al^{+3}$ and negatively charged moieties would provide prolonged inhibition of calcification in contradistinction to the short-lived effects of detergents and diphosphonates.

The term "biomaterial" as used herein denotes any biocompatible polymeric material, naturally derived, such as cellulose, or synthetic, whether hydrophilic or hydrophobic, including, without limitation, polydimethylsiloxane, polyurethane, ethylene vinyl acetate, polymethyl methacrylate, polyamide, polycarbonate, polyester, polyethylene, polypropylene, polystyrene, polyvinyl chloride, polytetrafluoroethylene, polysulfone, or cellulose acetate. The term "biomaterial" also specifically includes "bioprosthetic materials" such as bovine pericardium, porcine valve leaflets, aortic homografts, saphenous bypass grafts. It is to be understood that the term polymer is to be construed to include copolymers, such as the copolymer of polyurethane and silicone.

Given below are several specific illustrative techniques for producing calcification-resistant materials in accordance with the principles of the invention. Although the examples given are primarily directed to the preparation of calcification-resistant heart valves components, the techniques described herein are applicable to the creation of any other device, prothesis or implant comprising biomaterials of the type used for in-dwelling or surgically implanted devices.

TREATING BIOPROSTHETIC HEART VALVES

Bioprostheses such as porcine aortic valve leaflets or bovine pericardium are typically stabilized and preserved in glutaraldehyde following harvesting, illustratively a 0.2% solution of glutaraldehyde in 0.05M HEPES buffer (N-2-hydroxyethylpiperazine-N'-2-ethanesulfonic acid available from Sigma Chemical Co., St. Louis, MO). The glutaraldehyde-preserved bioprostheses can be stored at 4° C. for prolonged periods of time.

In accordance with one embodiment of the invention, glutaraldehyde-treated bioprosthetic tissue is incubated for a period of time, illustratively 24 hours, at a temperature ranging from the storage temperature (4° C.) to room temperature (25° C.) in an aqueous solution of a water-soluble aluminum compound that will ionize in solution to form trivalent aluminum cations. Following incubation, the bioprosthetic tissue is washed thoroughly (10×) with sterile, deionized water and then implanted in the subject.

An aqueous solution is recommended for bioprosthetic tissue inasmuch as organic solvents have deleterious effects on biologically-based tissue and could have toxic effects once implanted. However, an organic solvent is within the contemplation of the invention. Isopropanol, for example, has been used in connection with bioprosthetic tissues.

Water soluble aluminum salts, include without limitation, aluminum chlorate, aluminum lactate, aluminum potassium sulfate, aluminum sodium sulfate, aluminum sulfate, aluminum nitrate, and aluminum chloride. The examples herein are directed to aluminum chloride ($AlCl_3$). However, other compounds, such as aluminum lactate, would produce the same beneficial results and have a more neutral pH than $AlCl_3$.

In the specific $AlCl_3$ embodiment, a solution of the desired concentration is prepared in a fume hood by adding water to anhydrous $AlCl_3$ (Mallinckrodt, Inc. Paris, KY) over an ice bath with constant stirring due to the extremely exothermic nature of the reaction. $AlCl_3$ concentrations from 0.1M to 0.001M have been shown to be effective in the studies reported hereinbelow.

It should be noted that the aluminum chloride solution concentration range is given for purposes of illustration only, and can be varied by those of skill in the art because it is greatly in excess of the therapeutically effective amount. However, the ability to incorporate such a high concentration of trivalent aluminum cations in the bioprosthetic heart valve tissue, thereby placing a high concentration of drug at the potential site of calcification, is a significant advantage of this invention over the prior art.

TREATING HOMOGRAFT TISSUE

Homograft tissue is typically cryopreserved rather than glutaraldehyde-treated. After the tissue is thawed, the homograft tissue is then incubated in a sterile $AlCl_3$ solution for a period of time, illustratively an hour, prior to implantation. A shorter period of time is allotted for incubating the still viable homograft tissue than the devitalized bioprosthetic tissue.

PREPARATION OF SYNTHETIC MATERIALS

Trivalent aluminum cations may be incorporated into synthetic biomaterials as well.

A synthetic polymeric substrate material, such as medical grade polyurethane (sold under the trademark Thiomer by Thermedics Corp., Woburn, MA) is dissolved in a solvent, such as dimethylacetamide (DMAC) or tetrahydrofuran (THF), to form a clear homogenous solution. An aluminum compound is added to the liquid mixture. The aluminum compound should be chosen for its solubility and compatibility with both the polyurethane and the solvent.

In addition to dehydrated aluminum silicate, known as Kaolin, a variety of aluminum compounds can be incorporated into the polymeric substrate material. Other illustrative examples include aluminum oxide, aluminum phosphate, aluminum palmitate, aluminum oleate, aluminum oxalate, aluminum magnesium silicate, aluminum stearate, aluminum diacetate, aluminum hydroxide, aluminum isopropoxide, and aluminum hypophosphite.

In a preferred embodiment, dehydrated aluminum silicate, known as Kaolin, produced a satisfactory calcification-resistant polyurethane film. About 10% by weight Kaolin in DMAC-dissolved polyurethane was cast into thin polymer films on the order of 200 μm in thickness and dried in a vacuum oven at 55° C. with 2 millitorr pressure. The resulting polyurethane films were uniform, and demonstrated satisfactory elastic properties suitable for heart valve leaflets.

In addition to being cast as a film, the aluminum-containing synthetic polymeric material may be formed, such as by extrusion or compression molding, into a variety of configurations suitable for implantation or any other in-dwelling application where calcification is a risk. For example, the new synthetic polymer can easily be formed into heart valve leaflets, artificial heart device pumping bladders, detachable cardiac balloons, and the like. Of course, the material can also be applied as a coating or film, such as a coating to pacemaker leads.

Of course, the aluminum compound could also be incorporated in the polymeric matrix by other known material engineering techniques, such as by combining it with the polymeric precursors. In the Kaolin example given, combination of Kaolin with the polyurethane precursors assures its presence as the diisocyanate-polyether reaction goes to completion. Thus, the Kaolin is introduced as a primary ingredient in the solid phase polymerization.

One of the significant advantages of incorporating aluminum into the polymeric matrix is that it enables release of the anticalcification agent at a controlled rate over an extended period of time.

EXPERIMENTAL

A. Bioprosthetic Tissue in Rat Subdermal Model

Bioprosthetic tissue samples in the form of parietal pericardium from mature cows was obtained at slaughter and immediately placed in a 0.6% solution of glutaraldehyde in 0.05M HEPES buffer. After 24 hours, the tissue samples were transferred to 0.2% glutaraldehyde in HEPES and stored at 4° C. Using a #7 cork borer, the pericardium specimen was cut into 1 cm diameter pieces.

The bioprosthetic tissue was incubated in $AlCl_3$ solutions of various concentrations (0.001M, 0.01M, 0.1M) for 24 hours. The tissue was also incubated in non-aluminum ion containing solutions (pH 3.6 and pH 7.4) as controls. The acid control group was utilized because the pH of the $AlCl_3$ solutions is acidic.

The incubated bovine pericardium samples were implanted in two subcutaneous pouches dissected in the ventral abdominal wall of weanling rats (male, CD, Sprague-Dawley, weighing 50–60 gm). After periods of 21 and 60 days, the tissue samples were removed and examined for calcification by measuring the level of $Ca^{++}$ ions in the tissue. Tables 1 and 2 below summarizes the results where N refers to the number of rats in the treatment group.

Calcification of bioprosthetic tissue samples was markedly inhibited after both 21 day and 60 day implant intervals. More significantly, all concentrations of $Al^{+3}$ appeared to inhibit calcification to the same degree. The $Al^{+3}$ treatment also had no observable adverse effect on rat growth or bone morphology.

Reference to Tables 1 and 2 hows that the tissue calcium levels for the bioprosthetic specimens implanted for both 21 and 60 days was not significantly different. This is indicative the $Al^{+3}$ has that ability to afford long-term inhibition of calcification.

TABLE 1

| Tissue $Ca^{++}$ Levels at 21 Days Post-Implant | | |
|---|---|---|
| Treatment | N | Tissue $Ca^{++}$ (mg/mg) |
| 0.001M $AlCl_3$ | 10 | 3.5 + 1.8 |
| 0.01M $AlCl_3$ | 10 | 3.5 + 3.5 |
| 0.10M $AlCl_3$ | 12 | 3.8 + 0.5 |
| 0.001M HCL (pH 3.6) | 10 | 54.4 + 10.2 |
| 0.10M HEPES (pH 7.4) | 10 | 44.2 + 14.7 |

TABLE 2

| Tissue $Ca^{++}$ Levels at 60 Days Post-Implant | | |
|---|---|---|
| Treatment | N | Tissue $Ca^{++}$ (mg/mg) |
| 0.10M $AlCl_3$ | 8 | 4.13 + 1.03 |
| 0.001M HCL (pH 3.6) | 8 | 119.91 + 19.47 |
| 0.10M HEPES (pH 7.4) | 10 | 143.81 + 25.49 |

Compared to the two control groups, calcification was markedly inhibited in all groups which were pretreated with $Al^{+3}$-containing solutions. Of particular importance is the fact that this effect occurs even at extremely low concentrations of $AlCl_3$. Moreover, there was no observable adverse effect on calcium metabolism.

B. Rat Aortic Homograft Subdermal Studies

Thoracic aortas were removed from mature rats (male, CD, Sprague Dawley, Rattus norvegicus weighing between 200–300 g). The harvested aortas were split to completely expose the lumen and rinsed thoroughly with sterile, normal saline (0.9% NaCl).

Some of the thoracic aortas harvested were washed and incubated in $AlCl_3$ or control solutions, specifically, $AlCl_3$ solutions of the following concentrations: 0.01M; 0.001M; and 0.0001M; an acidic control solution (0.001M HCl, pH 3.0) and a physiologically buffered control solution (0.05M HEPES buffer, pH 7.4).

The aortic homograft samples were implanted in a subcutaneous pocket dissected in the ventral abdominal wall of weanling rats (50–60 g) of the same species. The rats received an injection of the antibiotic, chloramphenicol (100 mg/Kg/24° C.), for three days post-operation to prevent infection of the surgical wound.

The implanted homograft tissue samples were explanted after 21 days and were analyzed for calcium, aluminum, and evidence of morphological changes. Blood samples were obtained at sacrifice and analyzed for serum levels of calcium and aluminum. Bone samples (femurs) were removed from a representative sample of each group and fixed in 10% neutral buffered formalin for bone morphology assessment.

Calcium levels in untreated homografts showed a progressively increasing trend with time post-implant. The aluminum pretreatment inhibited calcification in the subdermal model. Table 3 shows calcium inhibition in homograft tissue samples which were explanted after 21 days. Referring to Table 3, a significant reduction of tissue calcium levels was observed for all $AlCl_3$ concentrations as compared to the controls. Serum calcium levels were not significantly different between $AlCl_3$ and control groups. Rat weight gains in the $AlCl_3$-treated groups and the acid control group were expressed as a percentage of the weight gain shown in the physiologically buffered control group for the 21 day period. None of the groups showed significant growth retardation.

TABLE 3

$Al^{+++}$ Inhibition of Aortic Homograft Calcification Rat (21 day, Male) Subcutaneous Implants - 3 Week Data*

| Group | N | Implant Ca++ (μg/mg) | Explant Ca++ (μg/mg) | Serum Ca++ (mg/dl) | Rat Wt Gain % of Control |
|---|---|---|---|---|---|
| 0.01M $AlCl_3$ | 5 | 0.80 ± 0.14 | 13.9 ± 4.9 | 12.3 ± 0.4 | 113 |
| 0.001M $AlCl_3$ | 5 | 0.91 ± 0.15 | 36.6 ± 7.1 | 13.6 ± 0.7 | 116 |
| 0.0001M $AlCl_3$ | 5 | 1.4 ± 0.07 | 114.5 ± 14.9 | 11.0 ± 0.4 | 110 |
| 0.001M HCL | 5 | 1.2 ± 0.27 | 159.8 ± 10.6 | 13.0 ± 0.9 | 118 |
| 0.05M HEPES | 5 | 1.2 ± 0.15 | 171.0 ± 13.2 | 13.0 ± 0.6 | 100 |
| Untreated Unimplanted | 5 | 0.77 ± 0.10 | — | — | — |

*Data as mean ± standard error

Aluminum levels in the homograft samples were measured prior to implantation and showed a greater concentration of $Al^{+3}$ than at explant. However, the two control groups showed a trend to greater $Al^{+3}$ concentration at explant than at implant. The amount of calcium accumulation was negatively correlated with the amount of $Al^{+3}$ present in the homografts at implant. Table 4 shows the $Al^{+3}$ and $Ca^{+2}$ content of aortic homograft specimens which were explanted after 21 days.

TABLE 4

$Al^{+++}$ Content of Aortic Homografts and Inhibition of Rat (21 day, Male) Subcutaneous Implants (3 wk) Calcification*

| Group | N | Explant Ca++ nM/mg | Implant $Al^{+++}$ nM/mg | Explant $Al^{+++}$ nM/mg |
|---|---|---|---|---|
| 10 nM/μl $AlCl_3$ | 5 | 346.7 ± 123 | 164.7 ± 4.9 | 65.3 ± 7.5 |
| 1 nM/μl $AlCl_3$ | 5 | 914.5 ± 178 | 49.8 ± 4.4 | 9.79 ± 1.1 |
| 0.1 nM/μl $AlCl_3$ | 5 | 2863 ± 372 | 20.5 ± 1.3 | 5.34 ± 0.30 |
| 1 nM/μl HCl | 5 | 3995 ± 265 | 0.83 ± 0.30 | 5.19 ± 0.56 |
| 50 nM/μl HEPES | 5 | 4275 ± 330 | 1.28 ± 0.72 | 5.67 ± 0.22 |
| Untreated Unimplanted | 5 | — | 0.29 ± 0.14 | — |

*Data as mean ± standard error

The foregoing examples and experimental results were given for the purpose of illustration only and are not to be construed as limiting the scope of the invention. Numerous and varied examples of the application of the principles of the invention can be devised by those of skill in the art without departing from the spirit and scope of the invention. Moreover, the examples cited do not preclude the use of other techniques for complexing trivalent aluminum cations with substrate biomaterial to achieve the goal of long-term incorporation of anti-calcification agents in implant materials.

The calcification-resistant material is ideally suited for body-invasive uses wherein pathologic calcification is a possibility. Such uses include, vascular grafts, pacemakers, numerous other prosthetic or implanted devices, such as artificial bone and hip joints, cosmetic implants of silicone, tendon protheses, etc.

What is claimed:

1. A method of treating glutaraldehyde pre-treated bioprosthetic tissue comprising incubating the bioprosthetic tissue in an aqueous solution of $AlCl_3$ ranging from 0.1M to 0.001M for a period of time ranging from 1 hour to 24 hours at about 4° C. to 25° C.

* * * * *